United States Patent
Outa et al.

(10) Patent No.: US 10,124,494 B2
(45) Date of Patent: Nov. 13, 2018

(54) COORDINATED WATER ENVIRONMENT MOBILE ROBOTS

(71) Applicant: Saudi Arabian Oil Company, Dhahran (SA)

(72) Inventors: Ali Outa, Thuwal (SA); Fadl Abdellatif, Dhahran (SA); Sahejad Patel, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/684,102

(22) Filed: Aug. 23, 2017

(65) Prior Publication Data

US 2018/0080307 A1    Mar. 22, 2018

Related U.S. Application Data

(60) Provisional application No. 62/397,175, filed on Sep. 20, 2016.

(51) Int. Cl.
*B25J 15/00* (2006.01)
*B63G 8/00* (2006.01)
(Continued)

(52) U.S. Cl.
CPC ............. *B25J 15/0028* (2013.01); *B08B 1/00* (2013.01); *B08B 3/024* (2013.01); *B08B 9/023* (2013.01); *B23K 31/125* (2013.01); *B25J 9/0009* (2013.01); *B25J 15/0009* (2013.01); *B63C 11/42* (2013.01); *B63C 11/52* (2013.01); *B63G 8/001* (2013.01); *B63G 8/14* (2013.01);
(Continued)

(58) Field of Classification Search
CPC ......... B63C 11/00; B63C 11/42; B63C 11/52; B60D 1/00; B60D 1/28; B60D 1/58; B63G 8/00; B63G 8/001; B63G 8/41; E21B 41/04; B25J 9/00
USPC .................................................. 114/312, 322
See application file for complete search history.

(56) References Cited

U.S. PATENT DOCUMENTS

| | | | |
|---|---|---|---|
| 2,427,129 A | 9/1947 | Fields | |
| 2,657,409 A | 11/1953 | Dawson | |
| 2,787,051 A | 4/1957 | Risley | |
| 4,552,594 A | 11/1985 | Van Vockuilen et al. | |
| 4,880,335 A | 11/1989 | Lee | |
| 5,097,780 A | 3/1992 | Winchester | |

(Continued)

FOREIGN PATENT DOCUMENTS

| | | |
|---|---|---|
| EP | 1030094 A2 | 8/2000 |
| EP | 2489911 A1 | 8/2012 |

(Continued)

*Primary Examiner* — Lars A Olson
(74) *Attorney, Agent, or Firm* — Leason Ellis LLP

(57) ABSTRACT

A two-part, selectively dockable robotic system having counterbalanced stabilization during performance of an operation on an underwater target structure is provided. The robotic system includes a first underwater robotic vehicle that is sized and shaped to at least partially surround the underwater target structure. A second underwater robotic vehicle is sized and shaped to at least partially surround the underwater target structure and selectively dock with the first underwater robotic vehicle. The first and second robotic vehicles include complimentary docking mechanisms that permit the vehicles to selectively couple to each other with the underwater target structure disposed at least partially therebetween. One robot includes a tool that can act upon the target structure and the other robot includes a stabilization module that can act upon the target structure in an opposite manner in order to counterbalance the force of the tool.

18 Claims, 5 Drawing Sheets

(51) Int. Cl.

| | | |
|---|---|---|
| *B63C 11/42* | (2006.01) | |
| *B63C 11/52* | (2006.01) | |
| *B63H 19/08* | (2006.01) | |
| *F16H 19/08* | (2006.01) | |
| *B63G 8/14* | (2006.01) | |
| *B23K 31/12* | (2006.01) | |
| *B63G 8/42* | (2006.01) | |
| *G01B 17/02* | (2006.01) | |
| *G01N 29/22* | (2006.01) | |
| *G01N 29/04* | (2006.01) | |
| *B25J 9/00* | (2006.01) | |
| *E21B 41/04* | (2006.01) | |
| *B08B 1/00* | (2006.01) | |
| *B08B 3/02* | (2006.01) | |
| *B08B 9/023* | (2006.01) | |
| *F16L 1/26* | (2006.01) | |
| *F16H 35/18* | (2006.01) | |
| *F16L 55/00* | (2006.01) | |
| *B62D 57/00* | (2006.01) | |

(52) U.S. Cl.
CPC ............... *B63G 8/42* (2013.01); *B63H 19/08* (2013.01); *E21B 41/04* (2013.01); *F16H 19/08* (2013.01); *F16H 35/18* (2013.01); *F16L 1/26* (2013.01); *G01B 17/02* (2013.01); *G01N 29/04* (2013.01); *G01N 29/225* (2013.01); *B62D 57/00* (2013.01); *B63G 8/00* (2013.01); *B63G 2008/002* (2013.01); *B63G 2008/005* (2013.01); *B63G 2008/008* (2013.01); *F16H 2019/085* (2013.01); *F16L 55/00* (2013.01); *G01N 2291/0234* (2013.01); *G01N 2291/02854* (2013.01); *G01N 2291/2675* (2013.01)

(56) References Cited

U.S. PATENT DOCUMENTS

| | | |
|---|---|---|
| 5,435,405 A | 7/1995 | Schempf et al. |
| 5,626,438 A | 5/1997 | Etheridge |
| 6,167,831 B1 | 1/2001 | Watt et al. |
| 6,523,629 B1 | 2/2003 | Buttz et al. |
| 7,000,560 B2 | 2/2006 | Wingett et al. |
| 7,656,997 B1 | 2/2010 | Anjelly |
| 7,992,508 B1 | 8/2011 | Norton |
| 8,619,134 B2 | 12/2013 | Christ |
| 2013/0062153 A1 | 3/2013 | Ben-Tzvi et al. |
| 2014/0230713 A1 | 8/2014 | Kimura et al. |
| 2015/0376851 A1 | 12/2015 | Yu et al. |

FOREIGN PATENT DOCUMENTS

| | | |
|---|---|---|
| GB | 957180 | 5/1964 |
| GB | 2027473 A | 2/1980 |
| GB | 2123073 A | 1/1984 |
| WO | WO 86/06696 | 11/1986 |
| WO | WO 2009/082240 A1 | 7/2009 |

COORDINATED WATER ENVIRONMENT MOBILE ROBOTS

CROSS-REFERENCE TO RELATED APPLICATIONS

This application claims priority under 35 U.S.C. §119 to U.S. Provisional Application Ser. No. 62/397,175, filed Sep. 20, 2016, which is hereby incorporated by reference as if set forth in its entirety herein.

FIELD OF THE INVENTION

Systems, methods and devices for performing inspection and other tasks on underwater assets including underwater pipelines and structures are provided that include or utilize at least first and second robots that are configured to cooperate with one another in support of an operation on a target pipeline or other structure.

BACKGROUND OF THE INVENTION

Underwater inspection operations can be a complicated task for a robotic system, especially when the task is performed while floating in water, for example, at a midpoint of the water column. Robotic manipulation of an inspection tool, such as an inspection arm, can be difficult as reaction forces from the inspected surface can push a remotely operated vehicle ("ROV") backward and disturb its stability. Similarly, performing marine life cleaning on an underwater pipe or pipeline, e.g., using a water jet, will create a strong push back making it difficult to stabilize the ROV.

Accordingly, there is a need to provide underwater vehicles that are structurally configured and operationally controlled to solve the stability issues associated with reaction forces caused by operation of tools, for instance, a robotic arm or a cleaning system (by way of example, and not limitation, a spinning brush or a cavitation/water jet). The present invention as described herein provides a solution to this and other problems.

SUMMARY OF THE INVENTION

In one aspect of the invention, a two-part, selectively dockable robotic system providing counterbalanced stabilization during performance of an operation on an underwater target structure is provided. The robotic system includes a first underwater robotic vehicle that is sized and shaped to at least partially surround the underwater target structure. A second underwater robotic vehicle that is sized and shaped to at least partially surround the underwater target structure is also provided. The second underwater robotic vehicle can be at least partially orientated in a position opposite the first underwater robotic vehicle. Complimentary docking mechanisms are supported by the first and second underwater robotic vehicles and arranged so the first and second underwater robotic vehicles can selectively couple to each other with the underwater target structure disposed at least partially between the first and second underwater robotic vehicles. A tool is provided that exerts a first force against the underwater target structure in a first direction. The tool can be supported by one of the first and second underwater robotic vehicles. A stabilization module is provided that exerts a second force against the underwater target structure in a second direction to at least partially counteract the first force. The stabilization module can be supported by one of the first and second underwater robotic vehicles.

According to a further aspect, the tool is a cleaning tool.

According to a still further aspect, the tool is a robotic arm.

According to another aspect, which can be combined in an embodiment constructed in accordance with one or more of the foregoing aspects, the stabilization module is a contact roller.

According to a further aspect, the stabilization module includes an inspection sensor.

According to a still further aspect, which can be combined in an embodiment constructed in accordance with one or more of the foregoing aspects, the docking mechanisms include a hook/protrusion and a receptacle, wherein the receptacle is sized and shaped to receive either the hook or the protrusion, as may be included in a particular embodiment.

According to a further aspect, which can be combined in an embodiment constructed in accordance with one or more of the foregoing aspects, the docking mechanisms include a latch and a protrusion, wherein the latch is operable to change positions to engage and disengage the protrusion.

According to a still further aspect, which can be combined in an embodiment constructed in accordance with one or more of the foregoing aspects, the docking mechanisms include moveable magnets that are operable to change pole orientations in order to engage and disengage with each other.

According to a further aspect, a method for performing a stabilized operation on an underwater target structure is provided. The method includes the steps of providing a two-part robotic system. The robotic system includes a first underwater robotic vehicle that is sized and shaped to at least partially surround the underwater target structure. A second underwater robotic vehicle that is sized and shaped to at least partially surround the underwater target structure is also provided. Complimentary docking mechanisms are supported by the first and second underwater robotic vehicles and arranged so the first and second underwater robotic vehicles can selectively couple to each other with the underwater target structure disposed at least partially between the first and second underwater robotic vehicles. A tool is provided that can be supported by one of the first and second underwater robotic vehicles. A stabilization module is provided that can be supported by one of the first and second underwater robotic vehicles. The method includes the step of coupling the first and second underwater robotic vehicles to each other with the underwater target structure disposed at least partially between the first and second underwater robotic vehicles. The tool is operated such that it exerts a first force against the underwater target structure in a first direction. The stabilization module is operated such that it exerts a second force against the underwater target structure in a second direction to at least partially counteract the first force.

According to a further aspect of the method, the tool is a cleaning tool.

According to a still further aspect of the method, the tool is a robotic arm.

According to another aspect of the method, which can be combined in an embodiment in accordance with one or more of the foregoing aspects, the stabilization module is a contact roller.

According to a further aspect of the method, the stabilization module includes an inspection sensor.

According to a still further aspect of the method, which can be combined in an embodiment in accordance with one or more of the foregoing aspects, the docking mechanisms include a hook/protrusion and a receptacle, wherein the receptacle is sized and shaped to receive either the hook or the protrusion, as may be included in a particular embodiment.

According to a further aspect of the method, which can be combined in an embodiment in accordance with one or more of the foregoing aspects, the docking mechanisms include a latch and a protrusion, wherein the latch is operable to change positions to engage and disengage the protrusion.

According to a still further aspect of the method, which can be combined in an embodiment in accordance with one or more of the foregoing aspects, the docking mechanisms include moveable magnets that are operable to change pole orientations in order to engage and disengage with each other.

DETAILED DESCRIPTION CERTAIN OF EMBODIMENTS OF THE INVENTION

Figure 1:
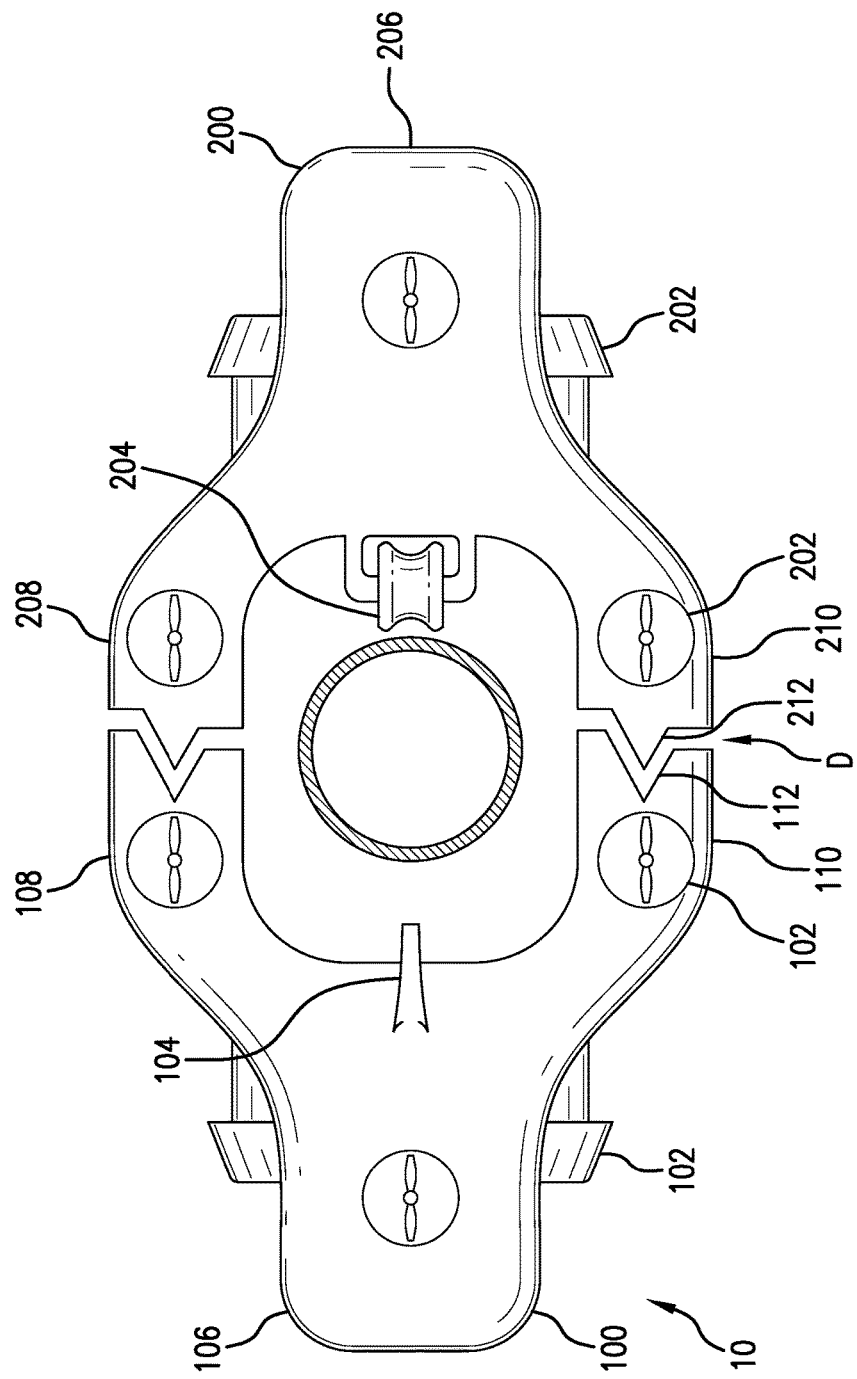
FIG. 1 illustrates coordinated water environment mobile robots in accordance with one embodiment of the present invention.

Referring to FIG. 1, a two part, selectively dockable robotic system 10 is provided. The robotic system 10 provides counterbalanced stabilization during performance of an operation (e.g., inspection, testing, cleaning, maintenance, construction, and repair) on an underwater target structure (e.g., pipe, cable, rig structure). The robotic system 10 includes first and second underwater robots 100, 200. The first and second underwater robots 100, 200 are controlled by a controller which is configured to coordinate their movements so that they cooperate and together improve the efficiency of various underwater tasks, as discussed in more detail below.

The first underwater robot 100 includes various thrusters 102 for maneuvering the robot 100 into position with respect to the target structure T. Once the robot 100 is in position, the thrusters 102 can be used to help maintain the position of the robot 100 and also translationally move the robot 100 along the target structure T and/or rotationally move the robot 100 around the target structure T as the robot performs tasks. The thrusters 102 can be aligned or otherwise rotated to align along different axes of the robot (e.g., x, y, and z axis) so that the robot can move in the three-dimensions in the underwater environment.

In FIG. 1, the target structure T is an exemplary underwater pipe. Other structures, such as cables, supports columns, tanks, anchoring chains, and other various marine infrastructure can be operated upon by the robot system 10; an underwater pipe is merely illustrated as an example target T.

The first robot 100 includes a tool 104 that is used to perform work upon the target structure T. For example, as shown in FIG. 1, the tool 104 can be a waterjet capable of expelling water at a rate of speed sufficient to dislodge bio-growth and other matter from the target T. Other tools, such as robotic arms, cleaning brushes, sensors, cameras, non-destructive inspection and testing equipment, sand blasters, welders, or other tools suitable for performing underwater inspection, testing, maintenance, cleaning, repair, or construction can also be used.

The first underwater robot 100 can have a hull structure 106 that is sized and shaped to at least partially surround the underwater structure T. For example, the underwater robot 100 can have a U-shaped hull that is sized and shaped for partially surrounding the structure T. As shown in FIG. 1, a U-shape hull is particularly suited for partially surrounding cylindrical objects, such as pipes. The hull 106 can have other sizes and shapes that can be designed to complement the target structure T. The hull 106 can include arms 108 and 110 that extend outwardly to at least partially encompass the target T and extend towards the second robot 200 and support first docking mechanisms 112 to facilitate docking between the two robots 100, 200, as discussed in more detail below.

The second underwater robot 200 can be similar to the first robot 100 in many respects. The second robot 200 can include a set of thrusters 202 for maneuvering into position and traversing the target structure T. The thrusters 202 can be aligned along different axes of the robot (e.g., x, y, and z axis) so that the robot can move in the three-dimensions in the underwater environment. The second robot 200 can have a hull 206 that has a similar size and shape to hull 106 of the first robot 100, including similar arms 208 and 210. Similarly, second docking mechanisms 212 can be supported by arms 208 and 210.

The second underwater robot 200 includes a stabilization module 204. As shown in FIG. 1, the stabilization module can comprise a roller that is arranged to contact the target structure T. Other devices, such as slides, bearings, skids, rollers, or other similar devices can be used to contact and apply a force against the target structure T. The stabilization module 204 provides a counterbalancing and stabilization force to the first robot 100 and the tool 104, as discussed in more detail below. Because the stabilization module 204 is in contact with the target structure T during operation of the tool 104, the stabilization module 204 can also include a sensor or other non-destructive testing equipment (e.g., camera, ultrasonic transducer, capacitive senor) that can inspect the condition of the target structure T. Accordingly, as the tool 104 performs operations on the target structure T (e.g., cleaning), the stabilization module 204 can provide a counterbalancing force and also can inspect the structure to confirm that the tool 104 has performed its operation satisfactorily or to signal when the intended operation performed by the tool is complete such that the robots 100, 200 can be removed from the target T or moved to a new location about a different target surface.

Cooperating component parts can be provided on the first and second underwater robots 100, 200 to provide a docking connector D that permits the robots to selectively couple with one another. The docking connector can include a first docking mechanism 112 supported by the first robot 100 and a second docking mechanism 212 supported by the second robot 200. The first docking mechanisms 112 are supported by arms 108 and 110 while and the second docking mechanism are supported by arms 208 and 210.

Figure 1A:
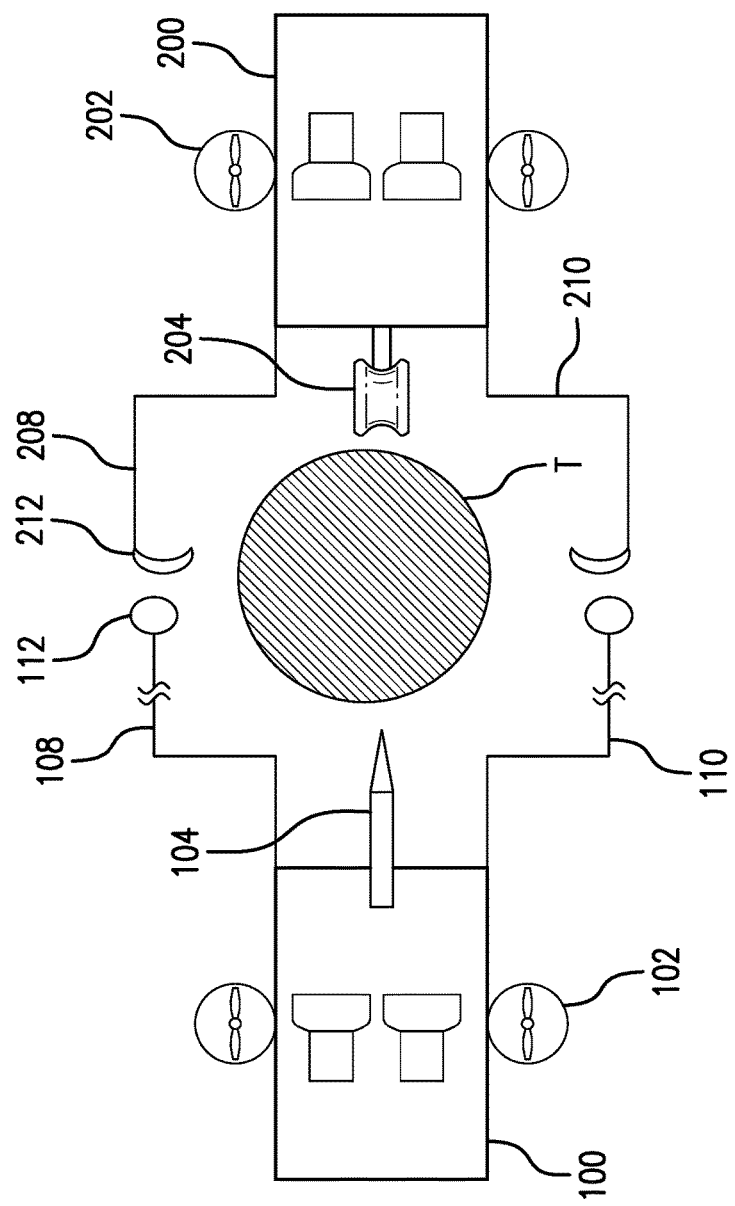
FIG. 1A is a schematic illustration of coordinated water environment mobile robots in accordance with an embodiment of the present invention

Turning briefly to FIG. 1A, a schematic representation of the arrangement of FIG. 1 illustrates the first and second underwater robots 100, 200 coupled together in surrounding relation to the underwater target T. The arms 108, 110, 208, and 210 can also be configured to extend in length (e.g., telescopically) or be in the form of ropes, chains, or cable, as illustrated schematically in FIG. 1A. Accordingly, the length of the arms can be adjusted so that first and second robots 100, 200 can dock together and accommodate target structures T of various sizes and shapes. As shown in FIG. 1A, the first docking mechanism 112 can be a receptacle, such as a ring, that is sized and shaped to receive the second docking mechanism 212, which can comprise a hook-shaped protrusion. The second docking mechanism 212 can be inserted into and retained by the first docking mechanism 112 to couple the first and second robots 100, 200 together. Other docking mechanism arrangements can be used, such as the docking mechanisms shown in FIGS. 2-4, which are discussed in more detail below. The thrusters 102, 202, and stabilization module 204 can be operated as described above.

When the first and second robots are coupled together via the docking mechanism they can at least partially surround the underwater target structure T. For example, the first and second robots 100, 200 can be sized and shaped to cross-sectionally surround the target structure T with the target structure T disposed between the robots, as shown in FIG. 1. In this configuration, the tool 104 is positioned for operation upon the target structure T and the stabilization mechanism 204 is positioned to provide a counterbalancing force to the forces exerted by the tool 104. As the tool 104 performs work upon the target structure (e.g., water jet cleaning), a force is exerted upon the target structure and an equal and opposite force is experienced by the first robot. This opposite reaction force can cause the first robot 100 to be pushed away from the target structure T. Without proper counteracting forces, the first robot 100 moves out of position and away from the target structure T and is either not be able to perform its task or not able to perform the task efficiently once displaced. The stabilization module 204 of the second robot 200 counteracts the reaction force experienced by the first robot 100. Thus, in accordance with the invention, because the first and second robots 100, 200 are coupled together, the first robot 100 is held in place as it works on the target structure by the second robot 200. As the tool 104 is operated it applies a first force against the target structure T and the stabilization module provides a second equal and opposite force that counteract the first force. Since the first and second robots 100, 200 are coupled together via the docking mechanisms, the net force experienced by the first and second robots 100, 200 is zero. The net zero force allows the robots to remain in a stable position with respect to the target structure T. Accordingly, the first and second robots and the active tool and the stabilization module work in concert to provide a stable working platform so that various operations can be performed on the target structure.

As an example, tool 104 can be a waterjet that blasts water at high pressure against the target structure T, which can be a pipe, as shown in FIG. 1. The waterjet can be directed onto the outer surface of the pipe to remove various debris, such as marine fouling and/or corrosion from the pipe surface. As the waterjet blasts against the surface of the pipe in one direction, the first robot experiences forces pushing it away from the pipe. Accordingly, the stabilization module 204, which can comprise a roller, contacts the other side of the pipe. The force of contact between the roller and the pipe surface is equal and opposite. These two forces are transmitted through the docking mechanism coupling the first and second robots 100, 200 together and cancel each other out. Accordingly, the robots remain stable with respect to the pipe and the cleaning operation can be performed efficiently in a controlled, stable manner.

In addition to being physically coupled together via the docking mechanisms, the first and second robots 100, 200 can also be coupled together so that control signals and other signals can be transmitted between the first and second robots. The robots can be connected via an electrical connection, which can be a part of the docking mechanism, and/or they can be connected via wireless communication modules (e.g., using Bluetooth®, near field communications, IEEE 802.11, or another communication protocol). Such a connection allows the robots to operate together in a coordinated-control fashion. For example, when the first robot moves along the target surface using its thrusters, it can provide control signals to the second robot to operate its thrusters in a complementary manner so that the first and second robots move in concert together. Accordingly, as the first robot moves along the target structure the second robot will follow and continue to provide the counterbalancing stabilization force required to maintain the robots in desired position with respect to the target structure.

According to one arrangement, communication can be established between the surface (e.g., a surface based control station, communication relay vehicle, or support vessel) and the first and second robots. The communication can be established using tethers (e.g., between the surface and the first and second robots) or a wireless technology (such as acoustics, laser, visible light, RF). Alternatively, a parent-child configuration could be used where a direct connection is established between the surface and a "main robot" (e.g. the first robot 100) using a tether, while the other "support robot" (e.g., the second robot 200) is then tethered to the main robot. This configuration reduces the number of tethers running to the surface. The connection between the two robots could also be accomplished using a short range wireless technology.

In one control scheme, the first and second robots can be independently controlled until they dock together. After docking is completed, the first and second robots can be configured to be remotely controlled as one unit to traverse the underwater target structure longitudinally or circumferentially.

Before docking, controllers on either robot can receive separate commands from the operator (e.g. joysticks) in order to actuate the correct thrusters to achieve the motion desired by the operator. To achieve the docking maneuver, one of the first and second robots (e.g., support robot) can be remotely controlled to rest against the underwater target structure (e.g., pipe) and optionally use sensors to automatically hold depth, orientation and/or position (using for example pressure sensor and compass). The operator and/or automatic controller provided by an onboard processor can also provide additional thrust force against the target structure surface to counteract recoil during docking.

The other of the first and second robots (e.g., main robot) is remotely controlled by the operator to maneuver it within vicinity of the support vehicle to initiate docking. Docking can then be performed manually by the operator or autonomously by the onboard controller on the main vehicle using onboard cameras or sonars or any suitable sensor to guide the docking maneuver. The controllers on both robots can also communicate with each in order to perform automatic corrections and thereby aid in the docking. The two robots can be remotely controlled in this manner at the same time or one after the other.

Once docking is completed, the operator can control the first and second robots as one unit in such way that the individual controllers associated with each of the first and second robots can exchange signals to determine which thrusters on the combined vehicle need to be actuated to achieve the desire motion by the operator including translation and rotation in any direction. Moreover, the controllers could also unlock extra degrees of freedom by using new combinations of thruster on both vehicles to achieve certain motions not possible by one vehicle due to restrictions on available thrusters.

Moreover, while performing a task, such as cleaning or inspection the controllers could automatically hold position by using the combined thrusters to correct for any longitudinal, circumferential or other displacements.

Once the task is completed, undocking can be performed. For example, the controllers can actuate their respective thrusters in opposite directions to undock. The controllers can also operate the docking mechanism to cause the first and second robotic vehicles to undock from each other. Independent manual control is regained over both the first and second robots after undocking is completed.

Figure 2A:
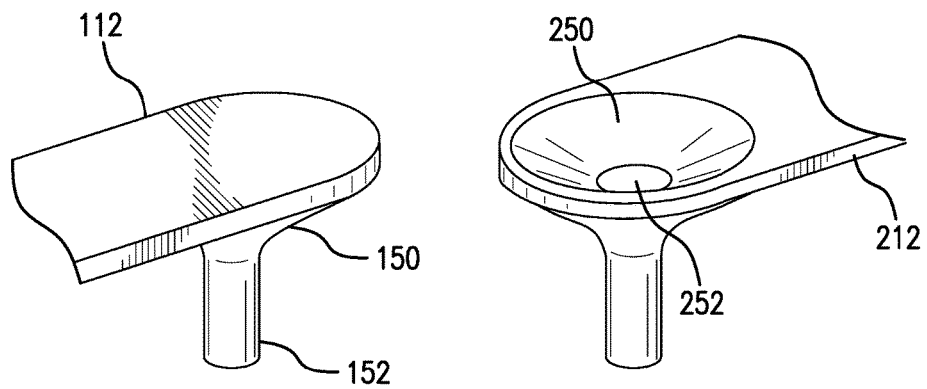
FIGS. 2A-2B illustrate a docking mechanism of coordinated water environment mobile robots in accordance with another embodiment of the present invention.
Figure 2B:
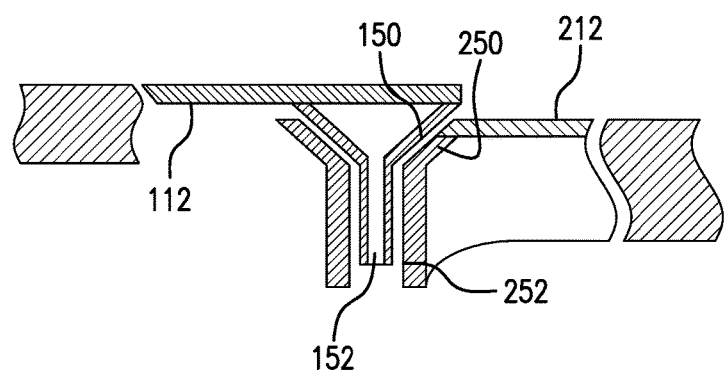

FIGS. 2A-2B show the first docking mechanism 112 of the first robot 100 and the second docking mechanism 212 of the second robot 200 according to a particular embodiment. The first docking mechanism 112 includes a protrusion that has a conically-shaped, flared portion 150 and an elongated post 152. The second docking mechanism 212 includes a receptacle that has a conically-shaped, flared portion 250 and an elongated hole 252 that are sized and shaped to receive the flared portion 150 and elongated portion 152 of the first docking mechanism 112, respectively, as shown in FIG. 2B. When the first docking mechanism 112 is received by the second docking mechanism 212, the first and second robots 100, 200 are coupled together (FIG. 2B).

Figure 3:
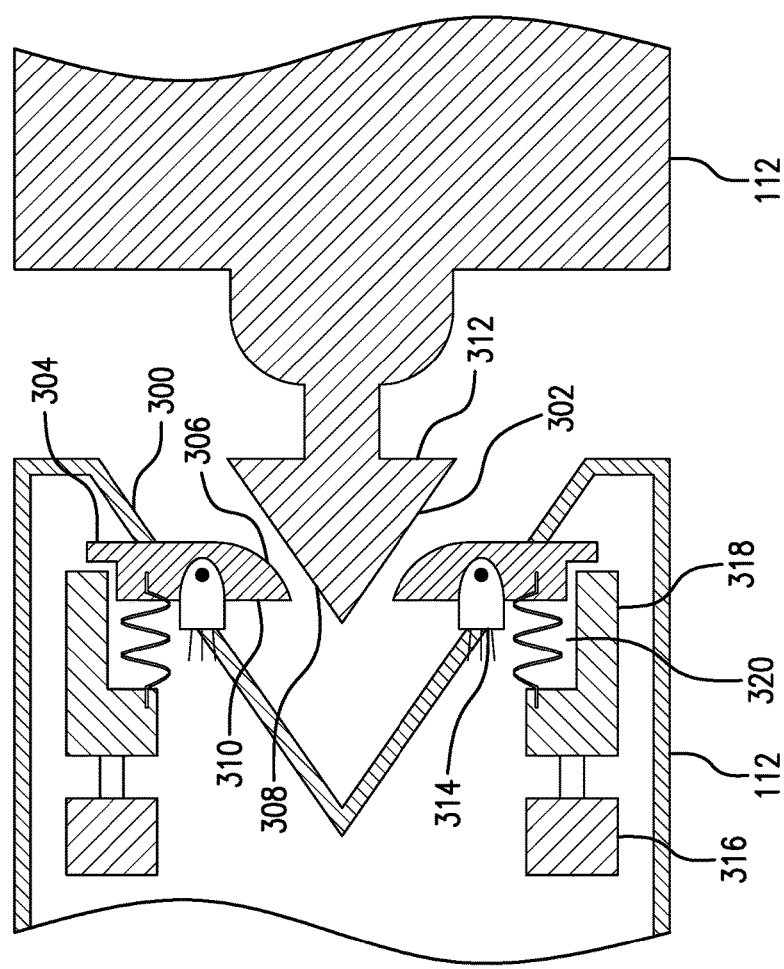
FIG. 3 illustrates a docking mechanism of coordinated water environment mobile robots in accordance with another embodiment of the present invention.

FIG. 3 shows the first docking mechanism 112 of the first robot 100 and the second docking mechanism 212 of the second robot 200 according to a particular embodiment. The first docking mechanism 112 includes a wedge-shaped receptacle 300 that is sized and shaped to receive the wedge-shaped protrusion 302 of the second docking mechanism 212. The first docking mechanism 112 includes two mechanically operable latches 304. The latches 304 include a sloping face 306 that is sized and shaped to compliment a forward edge 308 of the protrusion 302. As the protrusion 302 moves toward the receptacle 300 for docking, the complimentary surface 306 and 308 allow the parts to slide past each other more efficiently. The latches 304 include a generally flat surface 310 on a side opposite the sloping face 306. The protrusion 302 includes a shoulder 312 that as sized and shaped to receive the latches 304 with the flat surface 310 disposed adjacent the shoulder 312 when the first and second docking mechanisms 112, 212 are coupled.

The latches 304 are each supported by a pivot 314 and are connected for rotation about the pivot 314. An actuator 316, such as a solenoid, is connected to an arm 318 and is configured to extend and retract the arm 318 upon actuation of the actuator 316. The arm 318 is positioned with respect to the latch 304 to contact the latch when the actuator 316 is actuated into an extended position. The arm 318 includes a spring 320 that is connected to the latch 304 such that spring 320 exerts a pulling force upon the latch 304 upon retraction of the actuator 316. Since the latch is connected to the pivot 314, the actuation of the actuator 316 cause the latch 304 to rotate in both directions about the pivot 314. Accordingly, the actuator 316 can be actuated to rotate the latch 304 into a position to facilitate docking, rotated and maintained in position to maintain the robots in a docked configuration, and then rotated in an opposite direction to move the latch 304 so that the robots can decouple.

Figure 4A:
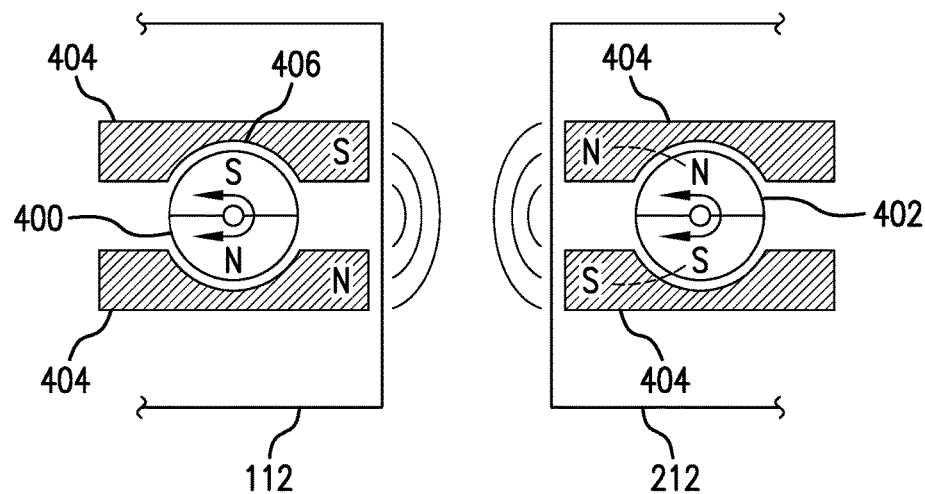
FIGS. 4A-4B illustrate a docking mechanism of coordinated water environment mobile robots in accordance with another embodiment of the present invention.
Figure 4B:
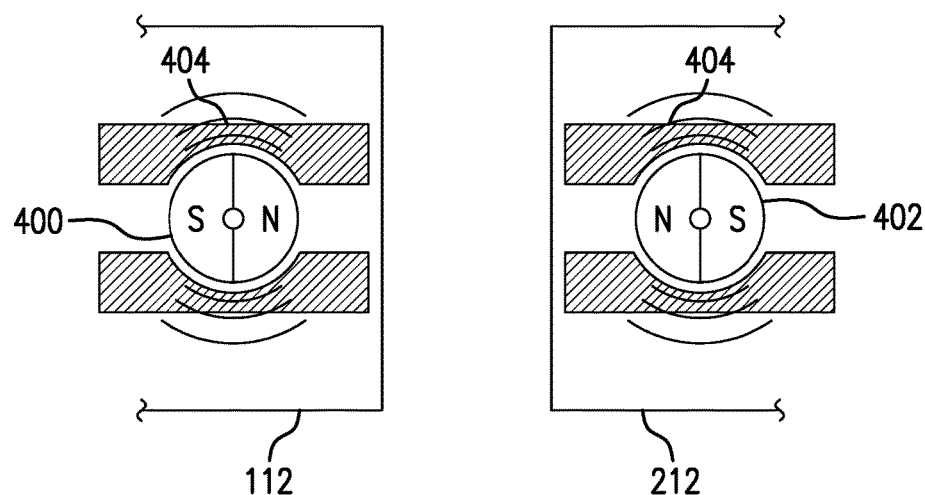

FIGS. 4A-4B illustrate the first docking mechanism 112 of the first robot 100 and the second docking mechanism 212 of the second robot 200 according to a particular embodiment. The docking mechanisms 112, 212 each include a motorized magnet 400, 402, respectively. The motorized magnets 400, 402 include a magnet having north and south poles that can be rotated so that the orientation of the north and south poles can be changed. Flux concentrators 404 are provided adjacent the motorized magnets 400, 402 so that the magnetic force of the magnet can be concentrated and directed toward opposing surfaces of the docking mechanisms 112, 212. The flux concentrators 404 can include recesses 406 that are sized and shaped to compliment the motorized magnets 400, 402 so that the space between the flux concentrators 400 and the motorized magnets 400, 402 can be minimized, thereby increasing the effectiveness of the flux concentrators.

As shown in FIG. 4A, the motorized magnets 400, 402 are oriented so that the poles are directed towards the flux concentrators 404. Motorized magnet 400 is oriented with its poles opposite the poles of motorized magnet 402. Accordingly, in this configuration, the docking mechanisms 112 and 212 experience an attractive magnetic force that facilitates and maintains coupling between the first and second robots 100, 200. Once docking is complete, the motorized magnets 400, 402 are rotated so that the poles are not directed toward the flux concentrators 404 and opposite poles are directed toward each other, as shown in FIG. 4B. Accordingly, no net magnetic force is directed through the flux concentrators 404 and the opposing poles of the magnets facilitate decoupling of the first and second robots 100, 200. Similarly, the motorized magnets 400, 402 can be rotated with the poles directed towards the flux concentrators 404 with the same pole orientation, causing a repulsive, decoupling force to be directed through the flux concentrators 404.

While the robots 100, 200 have been described as each having a tool 104 and a stabilization module 204, respectively, the tool 104 can be associated with the robot 100 and the stabilization module can be associated with the robot 200, as the robots described herein are otherwise the same, save for having complementary docking connector D features. As an alternative, the tools, stabilization module, and/or docking connector features can be supported one or the other of the first and second robots. Further, the first robot can be the "main robot" and the second robot can be the "support robot" and vise-a-versa. In an alternative embodiment, each of the robots 100, 200 can be provided with both a tool and a stabilization module, substantially as described above in connection with FIG. 1, in order to enable operations on either side of the target T with less rotation of the robots around the target. As will be appreciated, the particular tool and stabilization module construction included with a particular robot 100, 200 can be the same as included on the other robot, or different. By providing different tools on each of the robots 100, 200, a greater range of operations can be performed while the robots are underwater. In certain embodiments, the robots 100, 200 can include a tether and/or the robots can be docked with each other with a rope or chain. As the robots perform operation (cleaning and/or inspection) on the underwater target structure (e.g., helical sweep cleaning/inspection pattern) the tether/rope can wrap around the target structure. Once the operation is complete, the robots can perform a reverse maneuver that unwraps the tether/rope while also performing a second operation (cleaning and/or inspection).

It should be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present disclosure need not reside on a single computer or processor, but can be distributed in a modular fashion amongst a number of different computers or processors to implement various aspects of the systems and methods disclosed herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

Notably, the figures and examples above are not meant to limit the scope of the present application to a single implementation, as other implementations are possible by way of interchange of some or all of the described or illustrated elements. Moreover, where certain elements of the present application can be partially or fully implemented using known components, only those portions of such known components that are necessary for an understanding of the present application are described, and detailed descriptions of other portions of such known components are omitted so as not to obscure the application. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present application encompasses present and future known equivalents to the known components referred to herein by way of illustration.

The foregoing description of the specific implementations will so fully reveal the general nature of the application that others can, by applying knowledge within the skill of the relevant art(s) (including the contents of the documents cited and incorporated by reference herein), readily modify and/or adapt for various applications such specific implementations, without undue experimentation, without departing from the general concept of the present application. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the invention.

While various implementations of the present application have been described above, it should be understood that they have been presented by way of example, and not limitation. It would be apparent to one skilled in the relevant art(s) that various changes in form and detail could be made therein without departing from the spirit and scope of the application. Thus, the present application should not be limited by any of the above-described example implementations.

What is claimed:

1. A two-part, selectively dockable robotic system providing counterbalanced stabilization during performance of an operation on an underwater target structure, comprising:
    a first underwater robotic vehicle sized and shaped to at least partially surround the underwater target structure;
    a second underwater robotic vehicle sized and shaped to at least partially surround the underwater target structure and be at least partially orientated in a position opposite the first underwater robotic vehicle;
    complementary docking mechanisms supported by the first and second underwater robotic vehicles and arranged so the first and second underwater robotic vehicles can selectively couple to each other with the underwater target structure disposed at least partially between the first and second underwater robotic vehicles;
    a tool that exerts a first force against the underwater target structure in a first direction, the tool being supported by one of the first and second underwater robotic vehicles; and
    a stabilization module that exerts a second force against the underwater target structure in a second direction to at least partially counteract the first force, the stabilization module being supported by one of the first and second underwater robotic vehicles.

2. A two-part, selectively dockable robotic system according to claim 1, wherein the tool is a cleaning tool.

3. A two-part, selectively dockable robotic system according to claim 1, wherein the tool is a robotic arm.

4. A two-part, selectively dockable robotic system according to claim 1, wherein the stabilization module is a contact roller.

5. A two-part, selectively dockable robotic system according to claim 1, wherein the stabilization module includes an inspection sensor.

6. A two-part, selectively dockable robotic system according to claim 1, wherein the docking mechanisms include a hook and a receptacle, wherein the receptacle is sized and shaped to receive the hook.

7. A two-part, selectively dockable robotic system according to claim 1, wherein the docking mechanisms include a protrusion and a receptacle, wherein the receptacle is sized and shaped to receive the protrusion.

8. A two-part, selectively dockable robotic system according to claim 1, wherein the docking mechanisms include a latch and a protrusion, wherein the latch is operable to change positions to engage and disengage the protrusion.

9. A two-part, selectively dockable robotic system according to claim 1, wherein the docking mechanisms include moveable magnets that are operable to change pole orientations in order to engage and disengage with each other.

10. A method for performing a stabilized operation on an underwater target structure, comprising the steps of:
    providing a two-part robotic system, comprising:
        a first underwater robotic vehicle;
        a second underwater robotic vehicle;
        complementary docking mechanisms supported by the first and second underwater robotic vehicles and arranged so the first and second underwater robotic vehicles can selectively couple to each other with the underwater target structure disposed at least partially between the first and second underwater robotic vehicles;
        a tool, the tool being supported by one of the first and second underwater robotic vehicles; and
        a stabilization module, the stabilization module being supported by one of the first and second underwater robotic vehicles;
    coupling the first and second underwater robotic vehicles to each other with the underwater target structure disposed at least partially between the first and second underwater robotic vehicles;
    operating the tool such that it exerts a first force against the underwater target structure in a first direction; and
    operating the stabilization module such that it exerts a second force against the underwater target structure in a second direction to at least partially counteract the first force.

11. The method of claim 10, wherein the tool is a cleaning tool.

12. The method of claim 10, wherein the tool is a robotic arm.

13. The method of claim 10, wherein the stabilization module is a contact roller.

14. The method of claim 10, wherein the stabilization module includes an inspection sensor.

15. The method of claim 10, wherein the docking mechanisms include a hook and a receptacle, wherein the receptacle is sized and shaped to receive the hook.

16. The method of claim 10, wherein the docking mechanisms include a protrusion and a receptacle, wherein the receptacle is sized and shaped to receive the protrusion.

17. The method of claim 10, wherein the docking mechanisms include a latch and a protrusion, wherein the latch is operable to change positions to engage and disengage the protrusion.

18. The method of claim 10, wherein the docking mechanisms include moveable magnets that are operable to change pole orientations in order to engage and disengage with each other.

* * * * *

UNITED STATES PATENT AND TRADEMARK OFFICE
CERTIFICATE OF CORRECTION

PATENT NO.         : 10,124,494 B2
APPLICATION NO.    : 15/684102
DATED              : November 13, 2018
INVENTOR(S)        : Ali Outa et al.

It is certified that error appears in the above-identified patent and that said Letters Patent is hereby corrected as shown below:

On the Title Page

Item (72), Inventors:
"Hassane Trigui, Thuwal (SA)" should be added.

Signed and Sealed this
Sixteenth Day of July, 2019

Andrei Iancu
*Director of the United States Patent and Trademark Office*